United States Patent [19]
Hsieh

[11] Patent Number: 6,134,292
[45] Date of Patent: Oct. 17, 2000

[54] METHODS AND APPARATUS FOR REDUCING Z-AXIS NON-UNIFORMITY ARTIFACTS

[75] Inventor: Jiang Hsieh, Brookfield, Wis.

[73] Assignee: General Electric Company, Milwaukee, Wis.

[21] Appl. No.: 09/114,400

[22] Filed: Jul. 13, 1998

[51] Int. Cl.[7] ........................................ A61B 6/03
[52] U.S. Cl. ................... 378/4; 378/19; 378/901
[58] Field of Search ................... 378/4, 15, 19, 378/901

[56] References Cited

U.S. PATENT DOCUMENTS

| | | | |
|---|---|---|---|
| 5,473,656 | 12/1995 | Hsieh et al. ........................... | 378/4 |
| 5,734,691 | 3/1998 | Hu et al. ............................... | 378/4 |
| 5,867,553 | 2/1999 | Gordon et al. ........................ | 378/4 |

*Primary Examiner*—David V. Bruce
*Attorney, Agent, or Firm*—Armstrong Teasdale; Christian G. Cabou; Phyllis Y. Price

[57] ABSTRACT

Methods and apparatus of correcting image data for z-axis non-uniformity in a computed tomography (CT) system are described. In one embodiment, the CT system includes a configurable multislice detector array and a calibration algorithm. In accordance with one embodiment of the algorithm, output signals from a plurality of detector cells are sampled to generate an x-ray beam z-axis non-uniformity profile. The x-ray beam z-axis profile is then used to determine a detector z-axis non-uniformity profile for the detector array. Utilizing the z-axis profiles, the output signals from the detector cells may be calibrated to reduce z-axis non-uniformity errors.

48 Claims, 5 Drawing Sheets

METHODS AND APPARATUS FOR REDUCING Z-AXIS NON-UNIFORMITY ARTIFACTS

FIELD OF THE INVENTION

This invention relates generally to computed tomography (CT) imaging and more particularly, to correction of image data for z-axis non-uniformity error introduced into such data by x-ray beam and detector cell non-uniformity.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two-slice detector has two rows of detector elements, and a four-slice detector has four rows of detector elements. During a multislice scan, multiple rows of detector cells are simultaneously impinged by the x-ray beam, and therefore data for several slices is obtained.

In a CT system having such a 3-D detector, the intensity of detector measurements are derived by combining, along the z direction, multiple detector outputs. These outputs are supplied as inputs to a data acquisition system. If the detector outputs to be combined are obtained from detectors having different individual gains, the combined signal represents a weighted sum of the incoming detector signals where the different detector gains cause different weighting. Know gain calibration algorithms may be used to correct for this different weighting. However, these known calibration algorithms are unable to correct the signals when the error is caused by z-axis non-uniformity of the x-ray beam and the detector. As a result, a small variation in the non-uniformity of the z-response results in a substantial amount of artifacts in the reconstructed image.

It would be desirable to correct for z-axis non-uniformity of the x-ray beam to reduce image artifacts. It also would be desirable to more accurately generate an image regardless of the z-axis non-uniformity of the detector arrays. It further would be desirable to provide such imaging without significantly increasing the cost of the system.

SUMMARY OF THE INVENTION

These and other objects may be attained in a system which, in one embodiment, corrects the error in projection data resulting from z-axis non-uniformity of an x-ray beam and detector array. More particularly and in accordance with one embodiment, the present algorithm determines a z-axis non-uniformity profile for an incoming x-ray beam flux by fully sampling several channels of the detector array. Based on the fully sampled channels, a z-axis profile is generated for each of the sampled channels. Utilizing the z-axis profiles from the fully sampled channels, a z-axis profile is generated for the non-fully sampled channels. Specifically, as a result of the x-ray beam profile being a slowly varying function in the z-direction with respect to the channel number, the z-axis profile of the fully sampled channels may be used to generate z-axis profiles for the adjacent non-fully sampled channels.

In addition, the present algorithm determines a z-axis non-uniformity profile of the detector array by estimating the error caused by the gain variations of the individual detector array cells. Specifically, utilizing the z-axis profiles for the fully sampled channels, a detector cell z-axis non-uniformity profile may be generated for the detector array so that the output signals of the detector array may be calibrated to reduce z-axis non-uniformity errors.

The above described system enables correction of error due to z-axis non-uniformity of the x-ray beam and the detector array. Furthermore, the system enables correction of varying detector cell gain profiles. As a result, artifacts are reduced in a displayed image. The system also does not significantly increase the cost of the imaging system.

DETAILED DESCRIPTION OF THE DRAWINGS

Figure 1:
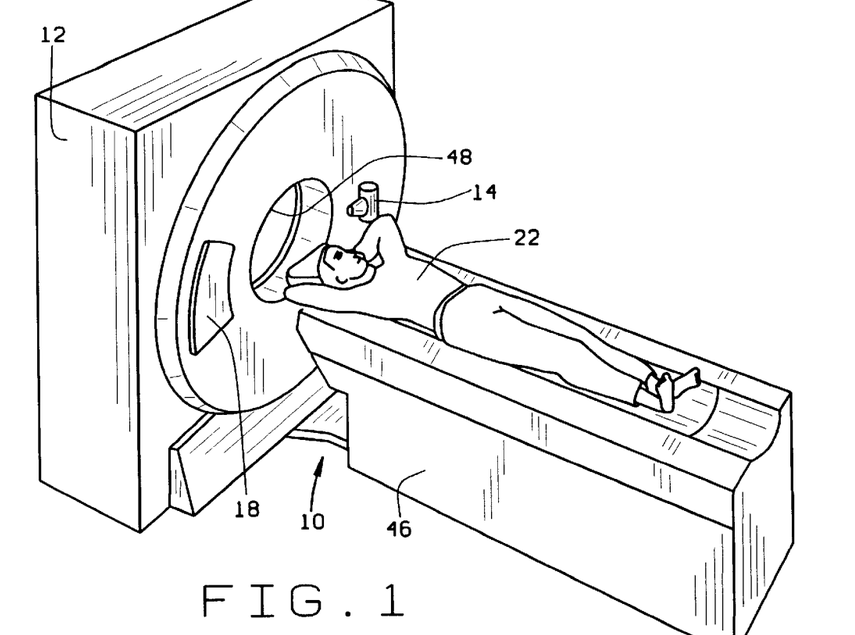
FIG. 1 is a pictorial view of a CT imaging system.
Figure 2:
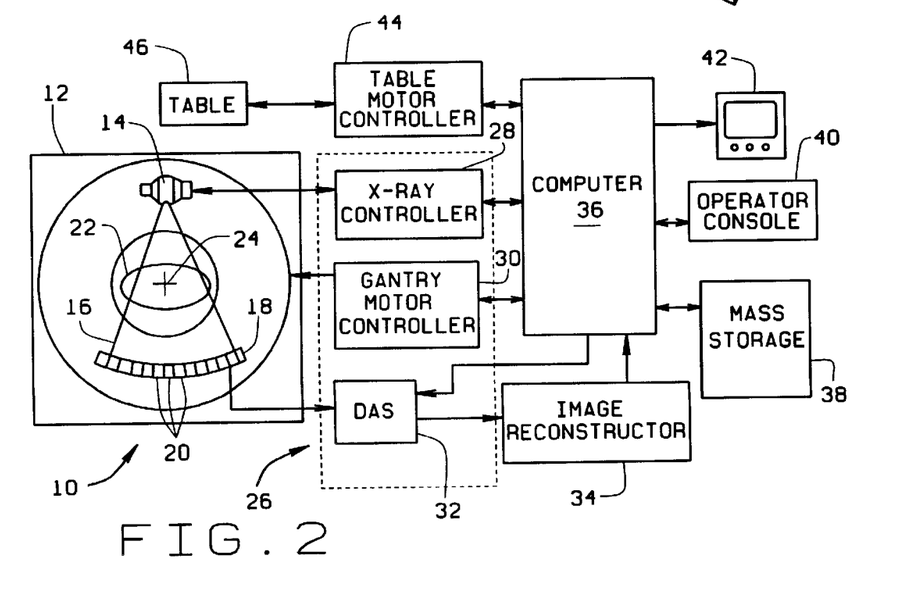
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion which describes correcting for z-axis non-uniformity sometimes refers specifically to an axial scan. The correction algorithm, however, is not limited to practice in connection with only axial scans, and may be used with other scans, such as helical scans. It should be further understood that the algorithm described below may be implemented in computer 36 and would process, for example, reconstructed image data. Alternatively, the algorithm could be implemented in image reconstructor 34 and supply corrected image data to computer 36. Other alternative implementations are, of course, possible.

Figure 3:
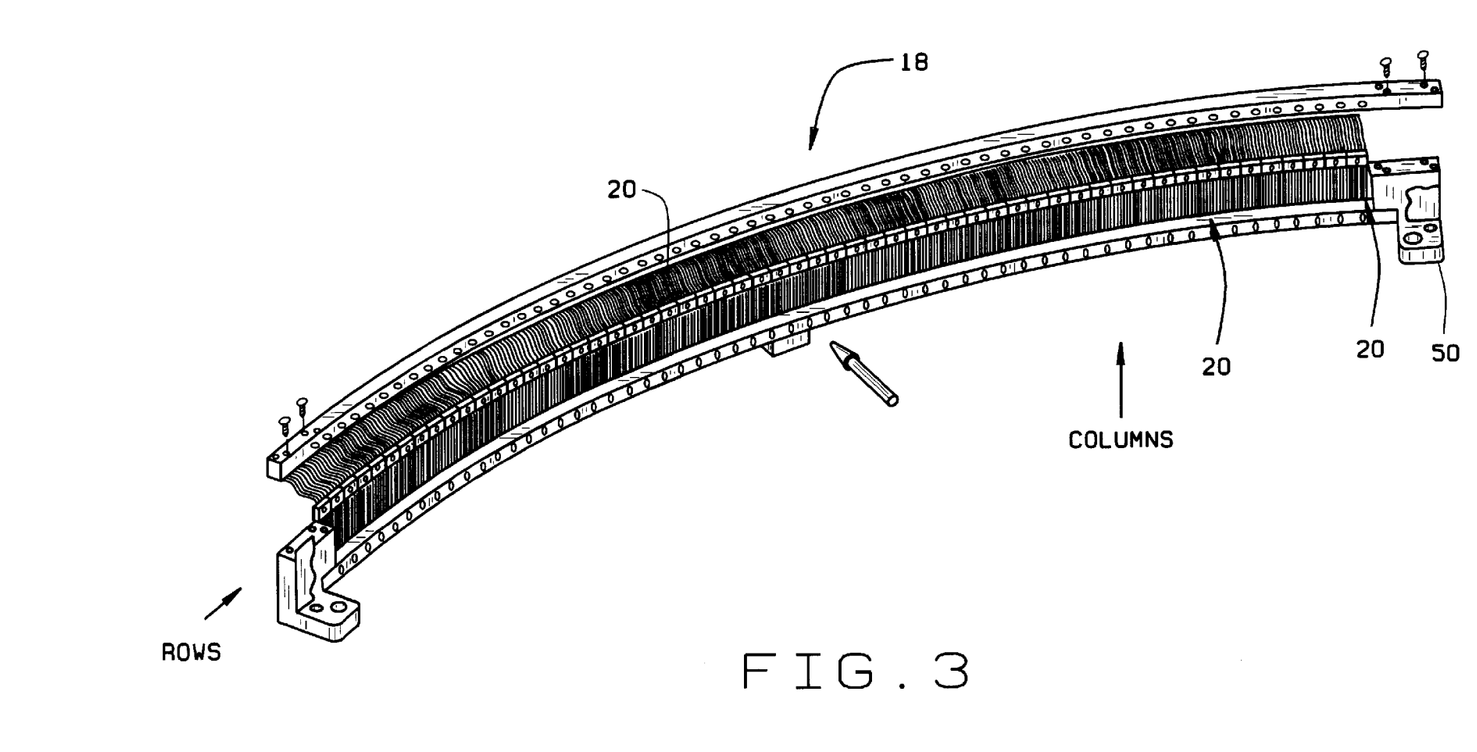
FIG. 3 is a perspective view of a CT system detector array.

As shown in FIG. 3, detector array 18 includes a plurality of detector modules 20 secured to an arc shaped detector housing 50. Each detector module 20 includes a multidimensional photodiode array (not shown) and a multidimensional scintillator array (not shown) positioned in front of and adjacent to the photodiode array. The photodiode array includes a plurality of photodiodes (not shown) which are optically coupled to the scintillator array. Each photodiode, identified as a cell, generates an electrical output signal representative of the light output by each scintillator of the scintillator array. In one embodiment, the cell output signals are supplied through a field effect transistor (FET) array (not shown) to DAS 32. By controlling the FET array, specific photodiode outputs are electrically supplied to DAS 32. In one embodiment where detector array 18 includes fifty-seven detector modules 20, with each detector module 20 including a photodiode array having 16 columns per channel, the FET array is configured so that all 16 output signals of the photodiode array, identified as a channel, are electrically supplied to DAS 32 to generate 16 simultaneous slices of data. Of course, many other combinations are possible.

For example, the FET array may be configured to provide other numbers of slices, including one, two, and four slice modes. Depending upon the specific configuration of the FET array various combinations of photodiode outputs may be enabled, disabled and combined so that the thickness of each slice may be 1, 2, 3, or 4 rows. Additional examples include, a single slice mode including one slice with slices ranging from 1 row to 16 rows thick; and a two-slice mode including two slices with slices ranging from 1 row to 8 rows thick. Additional modes beyond those described are possible where the total number of photodiode array element rows, or pixels per channel, is equal to the number of slices or FET array outputs times the number of rows per slice. For example, in a 4 slice mode of operation using 4 rows per slice, photodiode and scintillator arrays include at least 16 rows of cells and FET array includes at least four outputs. In one embodiment, for example, each row is 1.25 mm wide.

A calibration algorithm may be used to correct projection data for z-axis, or z-direction non-uniformity. Specifically, the calibration algorithm may be used to correct for z-axis non-uniformity of the x-ray beam and detector array 18. More specifically, utilizing the output signals of the photodiode array, separate z-axis non-uniformity profiles are generated for the x-ray beam and detector array 18.

Figure 4:
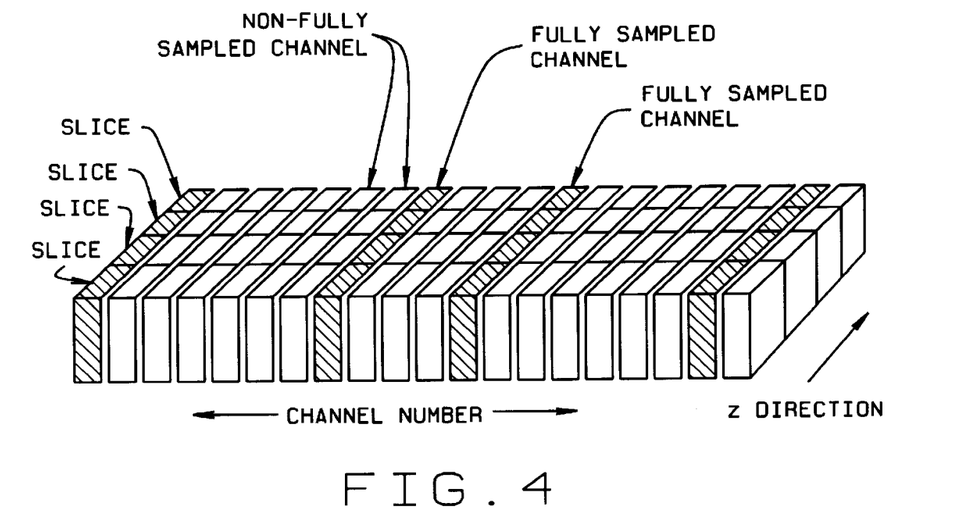
FIG. 4 illustrates a fully sampled channel and a non-fully sampled channel of the detector array of FIG. 3.

Referring to FIG. 4 and in one embodiment, the calibration algorithm generates the z-axis x-ray beam non-uniformity profile by obtaining, or sampling the output signals from at least one channel in the z-direction of detector array 18. Specifically, prior to combining the output signals with the FET array as determined by the configuration of detector array 18, the output signal from each detector cell of at least one channel, referred to as a fully-sampled channel, of array 18 is supplied to DAS 32. Utilizing the output signals from the fully sampled channel, a z-axis x-ray beam profile is determined for the channel. For example, where detector array 18 is configured to include four slices having a slice thickness of 5 mm (4–1.25 mm rows), the output signals are supplied to DAS 32 from each of the 16 cells in at least one channel for determining the z-axis x-ray beam profile. After the output signals are sampled, the output signals are combined to generate the four slice 5 mm images.

Using the output signals from a plurality of fully sampled channels, a z-axis profile may be generated for the entire x-ray beam. Specifically, by fully sampling a plurality of channel output signals a profile of the incoming x-ray beam flux may be estimated using various curve fitting and interpolation methods. More specifically because the incoming x-ray beam profile in the z-axis direction is a slowly varying function of the channel number, the z-axis profile variation can be assumed to be almost constant for a small group of channels adjacent to each fully sampled channel. Particularly and in one embodiment, the output signals from the fully sampled channels are interpolated to generate the x-ray beam z-axis profile for all non-fully sampled channels. Using the resulting x-ray beam z-axis profile, the output signal from each detector cell may be corrected for x-ray beam z-axis non-uniformity. In other embodiments, the x-ray beam z-axis profiles may be generated using curve fitting methods as well as assigning the fully sampled channel z-axis profile to non-fully sampled adjacent channels.

Figure 5:
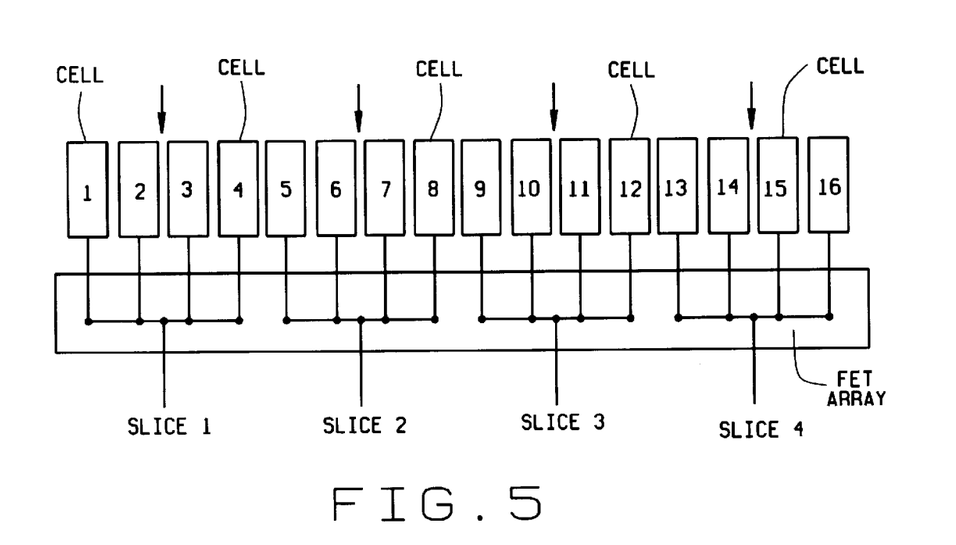
FIG. 5 illustrates detector cell data combining in a four-slice mode having 5 mm thickness image slices.
Figure 6:
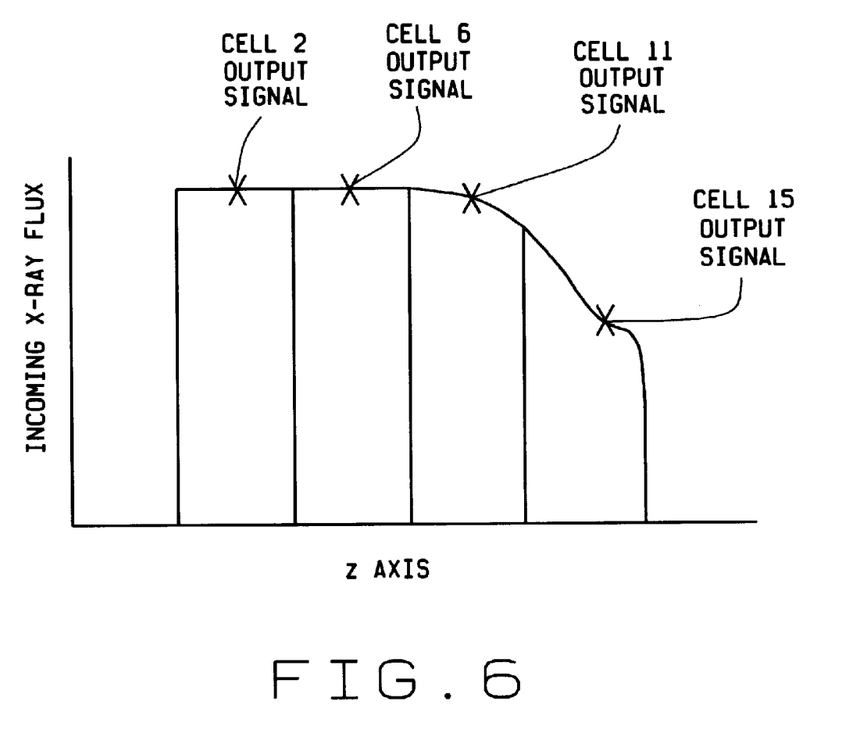
FIG. 6 illustrates a z-axis non-uniformity curve in accordance with one form of the present invention.

In an alternative embodiment, less than all of the detector cells in a selected channel are sampled. Specifically, after selecting the channels to be sampled, at least one cell of each slice is sampled to generate the x-ray beam z-axis profile. More specifically and in one embodiment shown in FIG. 5, where detector array 18 is configured in a four slice 5 mm thickness mode, prior to combining the output signals with the FET array, one output signal from each slice is supplied to DAS 32 for generating the x-ray beam z-axis profile. Particularly, prior to combining the output signals of respective cells 1 through 4, cells 5 through 8, cells 9–12, and cells 13–16 to generate data for respective slices 1, 2, 3, and 4, one output signal is sampled from respective cells 1 through 4, cells 5 through 8, cells 9–12, and cells 13–16. For example, output signals may be sampled from respective cells 2, 6, 11 and 15 to generate an x-ray beam z-axis profile for the sampled channel. For example, using a known curve fitting or technique and the output signals from cells 2, 6, 11 and 15, may result in an x-ray beam profile as shown in FIG. 6. Thereafter, by sampling multiple channels and using curve fitting or interpolation methods as described above, the sampled channel z-axis profiles may be used to generate z-axis profiles for the non-sampled channels.

Figure 7:
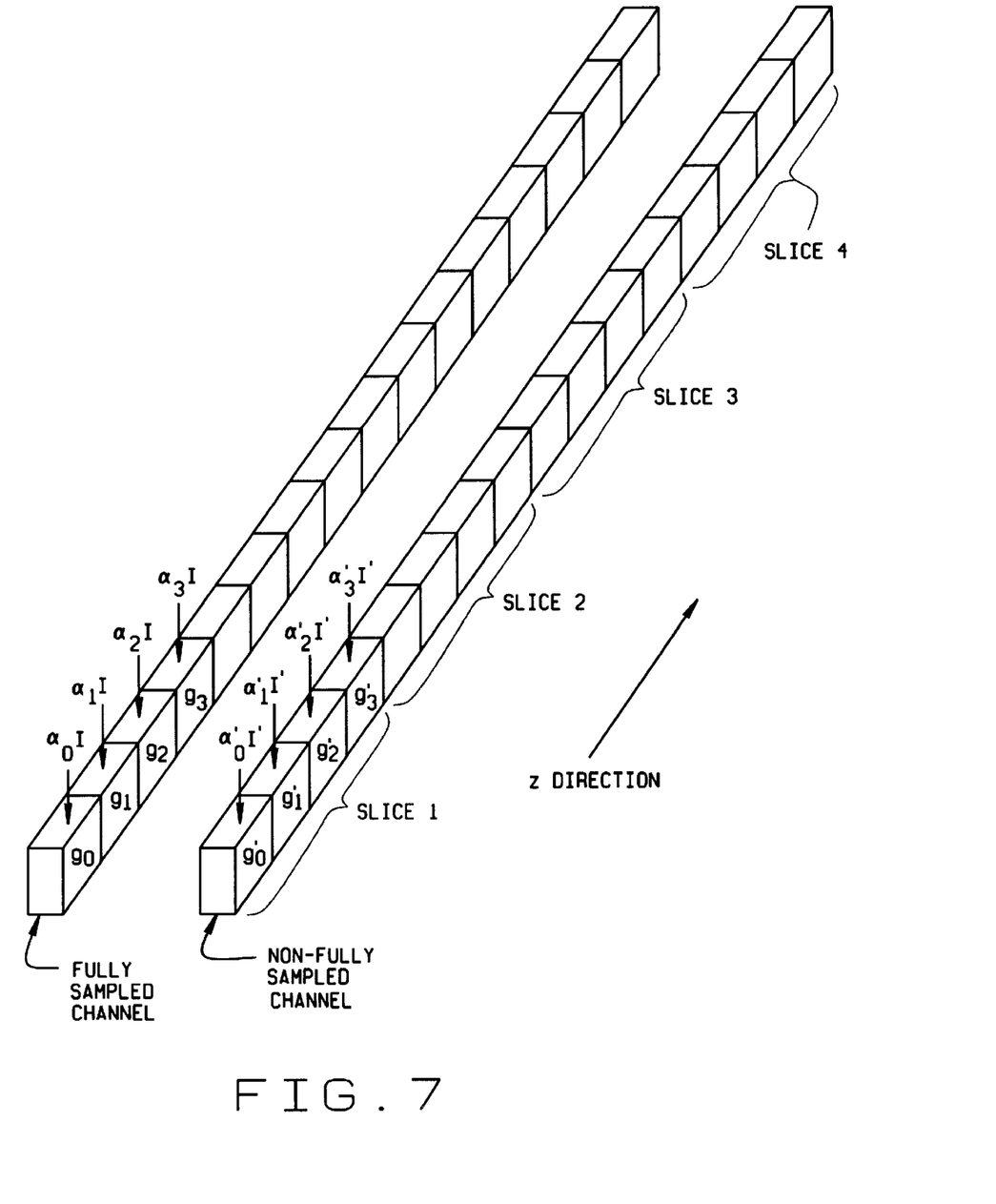
FIG. 7 illustrates two channels of the detector array shown in FIG. 4.

After determining the x-ray beam z-axis profile, the output signals for the configured slice and slice thickness mode are calibrated or adjusted based on the z-axis profile. Specifically, the measured output signals from the non-filly sampled channels are calibrated to adjust the signals for the z-axis profile. In one embodiment and as shown in FIG. 7, detector array 18 includes sixteen rows of cells and is configured in a four slice 5 mm thickness mode, where four 1.25 mm cells are combined to form one 5 mm cell. More specifically and referring to slice 1, the gains for the fully sampled cells are $g_0$, $g_1$, $g_2$, $g_3$ and the variations of x-ray flux in the z-direction, or x-ray beam z-axis profile, are $\alpha_0 I$, $\alpha_1 I$, $\alpha_2 I$, $\alpha_3 I$. Corresponding parameters for non-fully sampled cells are $g'_0$, $g'_1$, $g'_2$, $g'_3$, $\alpha'_0 I'$, $\alpha'_1 I'$, $\alpha'_2 I'$, and $\alpha'_3 I'$. The parameters $g'_0$, $g'_1$, $g'_2$, $g'_3$ may be generated using known gain calibrations for the non-fully sampled channels. As described above, $\alpha'_0$, $\alpha'_1$, $\alpha'_2$, and $\alpha'_3$ may be generated using interpolation, curve fitting or may be assigned the values of adjacent fully sampled cells. The measured output signal from a non-fully sampled channel y' is:

$$y' = \sum_{i=0}^{M} g'_i \alpha'_i I'$$

where:

$I'$ = average x-ray intensity of a non-fully sampled cell, $g'_i$ = gain of non-fully sampled channel cell i, $\alpha'_i$ = x-ray beam z-profile variation on cell i.

Specifically, and in one embodiment, detector array 18 is configured in a four slice mode, where four 1.25 mm cells are combined to form a 5 mm slice, the measured output signal from a non-fully sampled channel, y', is:

$$y' = g'_0 \alpha'_0 I' + g'_1 \alpha'_1 I' + g'_2 \alpha'_2 I' + g'_3 \alpha'_3 I'.$$

The true x-ray flux to the channel, x', is:

$$x' = \frac{\sum_{i=0}^{M} \alpha'_i}{\sum_{i=0}^{M} g'_i \alpha'_i} y'.$$

In the four 5 mm slice mode described above, the true x-ray flux to a non-fully sampled channel, x', is:

$$x' = \frac{\alpha'_0 + \alpha'_1 + \alpha'_2 + \alpha'_3}{g'_0 \alpha'_0 + g'_1 \alpha'_1 + g'_2 \alpha'_2 + g'_3 \alpha'_3} y'.$$

The true x-ray flux and measured output signals are similarly determined for other slices, for example, slices 2, 3 and 4.

As a result of the slowly varying z-profile variation, the α parameters can be estimated on multiple views or an average of multiple views to reduce the influence of statistical fluctuation. In addition, the use of multiple views reduces the computational burden of the correction algorithm.

Various methods may be used to determine which cells may be sampled to determine the z-axis profiles for the x-ray beam and detector array 18. In one embodiment where multiple channels are fully sampled, the z-axis uniformity of the channels may be utilized to determine the spacing of the fully sampled channels. Specifically, because the center channels are more sensitive to z-axis non-uniformity, the spacing of the channels to be fully sampled are closer together near the iso-center channel and farther apart away from the iso-center channel. In another embodiment, information from adjacent channels may be used to generate the z-axis profile so that the error introduced from any one cell is minimized.

In an additional embodiment, only those detector cells known to have uniform gain measurements are manually selected for generation of the z-axis profile. Specifically, because the output of these uniform gain channels have no error, the channel is not required to be fully sampled. Utilizing these cells, $\alpha_0$, $\alpha_1$, $\alpha_2$, and $\alpha_3$ may be estimated based on a polynomial fit of the measured signal from the uniform gain cells. After estimating the measured signal, interpolation, or one of the other methods described above, may be utilized to estimate $\alpha'_0$, $\alpha'_1$, $\alpha'_2$, $\alpha'_3$ for the non-uniform cells.

In another additional embodiment, an estimate of the x-ray beam incoming flux profile is generated and used to calibrate the detector cells output signals. The calibrated measurements of the detector cells are then used to generate a revised x-ray beam z-axis profile.

The above described system includes a calibration algorithm for correction of error due to z-axis non-uniformity of the x-ray beam and the detector array. In addition, the system enables correction of varying detector cell gain profiles. As a result, artifacts are reduced in a displayed image.

From the preceding description of several embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. The present invention, however, may be used with many other CT systems including "fourth generation" systems wherein the detector is a full-ring stationary detector and only the x-ray source rotates with the gantry. The present invention could also be utilized in connection with stop-and-shoot as well as helical scanning type CT systems. In addition, although the correction algorithm, in one form, has been described being performed on data directly from the output signals, the present invention could be implemented at various points in the data correction/processing process. Accordingly, the spirit and scope of the invention are to be limited only by the terms of the appended claims.

What is claimed is:

1. A system for calibrating projection data for generating a tomographic image of an object, said system comprising an x-ray source and a detector array comprising a plurality of cells arranged in rows and columns and displaced along a z-axis, the detector array column cells being arranged in channels, said system being configured to:
   determine an x-ray beam z-axis profile; and
   determine a true x-ray flux utilizing detector gain profiles and the determined x-ray beam profile;
   wherein:
   said system being configured to determine an x-ray beam z-axis profile comprises said system being configured to obtain signals from a select number of detector cells in at least one channel of the detector array; and
   said system being configured to obtain signals from a selected number of detector cells comprises said system being configured to select at least one detector cell having a uniform gain measurement.

2. A method for calibrating projection data in a multi-slice computed tomography system, the system including an x-ray source and a detector array comprising a plurality of cells arranged in rows and columns and displaced along a z-axis, and the detector array cells are arranged in channels, said method comprising the steps of:
   determining an x-ray beam z-axis profile including obtaining signals from detector cells in at least one fully sampled channel of the detector array; and
   determining a true x-ray flux utilizing detector gain profiles and the determined x-ray beam profile.

3. A method in accordance with claim 2 wherein each channel comprises a plurality of slices.

4. A method in accordance with claim 3 wherein determining an x-ray beam z-axis profile comprises fully sampling a plurality of channels and interpolating signals from the fully-sampled channels to estimate an x-ray beam z-axis profile for non-fully-sampled channels.

5. A method in accordance with claim 2 further comprising the step of determining a gain profile for each of the selected detector cells to determine detector gain profiles.

6. A method in accordance with claim 2 further comprising the step of adjusting the projection data using the detector gain profiles and x-ray flux profiles.

7. A method in accordance with claim 6 wherein adjusting projection data comprises the step of generating a gain profile for each detector cell not fully sampled.

8. A method in accordance with claim 7 wherein generating a gain profile for each non-fully-sampled detector cell comprises the step of determining a measured output signal, wherein the measured output signal, y', is:

$$y' = \sum_{i=0}^{M} g'_i \alpha'_i I'$$

where:

$g'_i$ = gain of cell i in detector channel;

$\alpha'_i$ = variation of flux in z direction on cell i;

$I'$ = average x-ray intensity of a non-fully sampled cell;

and $M$ = number of cells that form a slice.

9. A method in accordance with claim 8 wherein generating the true x-ray flux for each non-fully-sampled detector cell further comprises the step of determining a true x-ray flux for the channel.

10. A method in accordance with claim 9 wherein the true x-ray flux for the channel is:

$$x' = \frac{\sum_{i=0}^{M} \alpha'_i}{\sum_{i=0}^{M} g'_i \alpha'_i} y'.$$

11. A method in accordance with claim 10 wherein each slice channel comprises four cells and wherein the measured output signal for each slice of each non-fully-sampled detector cell is:

$$y' = g'_0 \alpha'_0 I' + g'_1 \alpha'_1 I' + g'_2 \alpha'_2 I' + g'_3 \alpha'_3 I'.$$

12. A method in accordance with claim 10 wherein the true x-ray flux for the channel is:

$$x' = \frac{\alpha'_0 + \alpha'_1 + \alpha'_2 + \alpha'_3}{g'_0 \alpha'_0 + g'_1 \alpha'_1 + g'_2 \alpha'_2 + g'_3 \alpha'_3} y'.$$

13. A method in accordance with claim 12 wherein generating the x-ray flux profile for the non-fully-sampled detector cells comprises the step of creating a polynomial fit of the fully-sampled detector cell output signals.

14. A method in accordance with claim 2 wherein obtaining signals from detector cells in at least one fully sampled channel of the detector array further comprises the steps of:
   generating view data utilizing the detector cell signals; and
   generating the true x-ray flux profile utilizing the view data.

15. A method in accordance with claim 2 wherein obtaining signals from detector cells in at least one fully sampled channel of the detector array further comprises the steps of:
   generating data for multiple views utilizing the detector cell signals; and
   generating the true x-ray flux profile utilizing the multiple view data.

16. A method in accordance with claim 2 wherein obtaining signals from detector cells in at least one fully sampled channel of the detector array further comprises the step of selecting at least one detector cell having an uniform gain measurement.

17. A method in accordance with claim 2 wherein determining an x-ray beam z-axis profile comprises the steps of:
   estimating an x-ray flux profile;
   adjusting the output signals of each channel; and
   generating a revised x-ray beam z-axis profile utilizing the adjusted output signals.

18. A system for calibrating projection data for generating a tomographic image of an object, said system comprising an x-ray source and a detector array comprising a plurality of cells arranged in rows and columns and displaced along a z-axis, the detector array column cells being arranged in channels, said system being configured to:
   determine an x-ray beam z-axis profile; and
   determine a true x-ray flux utilizing detector gain profiles and the determined x-ray beam profile;
   wherein:
   said system being configured to determine an x-ray beam z-axis profile comprises said system being configured to obtain signals from a select number of detector cells in at least one channel of the detector array;

said system being configured to determine an x-ray beam z-axis profile comprises said system being configured to:

estimate an x-ray flux profile;

adjust the output signals of each channel; and generate a revised x-ray beam z-axis profile utilizing the adjusted output signals.

19. A system for calibrating projection data for generating a tomographic image of an object, said system comprising an x-ray source and a detector array comprising a plurality of cells arranged in rows and columns and displaced along a z-axis, wherein said detector cell columns are arranged in channels said system configured to:

determine at least one z-axis x-ray beam profile; and determine a true x-ray flux utilizing detector gain profiles and said determined x-ray beam profile;

and wherein to determine said x-ray beam profile, said system is configured to obtain signals from a select number of detector cells in at least one channel of said detector array.

20. A system in accordance with claim 19 wherein each channel comprises a plurality of slices.

21. A system in accordance with claim 20 wherein said system being configured to determine an x-ray beam z-axis profile comprises said system being configured to fully sample a plurality of channels and to interpolate signals from the fully-sampled channels to estimate an x-ray beam z-axis profile for non-fully-sampled channels.

22. A system in accordance with claim 19, said system being further configured to determine a gain profile for each of said selected detector cells.

23. A system in accordance with claim 19 further configured to adjust the projection data using said detector gain profiles and said x-ray flux.

24. A system in accordance with claim 23 wherein to adjust the projection data, said system is configured to generate a gain profile for each detector cell not fully sampled.

25. A system in accordance with claim 24 wherein to generate a gain profile for each non-fully-sampled detector cell, said system is configured to determine a measured output signal, wherein said measured output signal, y', is:

$$y' = \sum_{i=0}^{M} g'_i \alpha'_i I'$$

where:

$g'_i$ = gain of cell i in detector channel;

$\alpha'_i$ = variation of flux in z direction on cell i;

$I'$ = average x-ray intensity of a non-fully sampled cell;

and $M$ = number of cells that form a slice.

26. A system in accordance with claim 25 wherein to generate said true x-ray flux for each non-fully-sampled detector cell, said system is configured to determine a true x-ray flux for said channel.

27. A system in accordance with claim 26 wherein said true x-ray flux for said channel is:

$$x' = \frac{\sum_{i=0}^{M} \alpha'_i}{\sum_{i=0}^{M} g'_i \alpha'_i} y'.$$

28. A system in accordance with claim 27 wherein each slice channel comprises four cells and wherein said measured output signal for each slice of each non-fully-sampled detector cell is:

$$y' = g'_0 \alpha'_0 I' + g'_1 \alpha'_1 I' + g'_2 \alpha'_2 I' + g'_3 \alpha'_3 I'.$$

29. A system in accordance with claim 27 wherein said true x-ray flux for said channel is:

$$x' = \frac{\alpha'_0 + \alpha'_1 + \alpha'_2 + \alpha'_3}{g'_0 \alpha'_0 + g'_1 \alpha'_1 + g'_2 \alpha'_2 + g'_3 \alpha'_3} y'.$$

30. A system in accordance with claim 29 wherein to generate said x-ray flux profile for said non-fully-sampled detector cells, said system is configured to create a polynomial fit of said fully-sampled detector cell output signals.

31. A system in accordance with claim 19 wherein to obtain signals from detector cells in at least one fully sampled channel of the detector array, said system is further configured to:

generate view data utilizing said detector cell signals; and generate said true x-ray flux profile utilizing said view data.

32. A system in accordance with claim 19 wherein to obtain signals from detector cells in at least one fully sampled channel of the detector array, said system is further configured to:

generate data for multiple views utilizing said detector cell signals; and generate said true x-ray flux profile utilizing said multiple view data.

33. A system in accordance with claim 19 wherein to obtain signals from detector cells in at least one fully sampled channel of the detector array, said system is further configured to select at least one detector cell having an uniform gain measurement.

34. A system in accordance with claim 19 wherein to determine an x-ray beam z-axis profile, said system is configured to:

estimate an x-ray flux profile;

adjust said output signals of each channel; and generate a revised x-ray beam z-axis profile utilizing said adjusted output signals.

35. A method for calibrating projection data in a multislice computed tomography system, the system including an x-ray source and a detector array comprising a plurality of cells arranged in rows and columns and displaced along a z-axis, the detector array column cells being arranged in channels, said method comprising the steps of:

determining an x-ray beam z-axis profile, including obtaining signals from a select number of detector cells in at least one channel of the detector array; and determining a true x-ray flux utilizing detector gain profiles and the determined x-ray beam profile;

wherein obtaining signals from a selected number of detector cells comprises the step of selecting at least one detector cell having a uniform gain measurement.

36. A method for calibrating projection data in a multislice computed tomography system, the system including an x-ray source and a detector array comprising a plurality of cells arranged in rows and columns and displaced along a z-axis, the detector array column cells being arranged in channels, said method comprising the steps of:

determining an x-ray beam z-axis profile, including obtaining signals from a select number of detector cells in at least one channel of the detector array; and determining a true x-ray flux utilizing detector gain profiles and the determined x-ray beam profile;

wherein determining an x-ray beam z-axis profile comprises the steps of:

estimating an x-ray flux profile;

adjusting the output signals of each channel; and generating a revised x-ray beam z-axis profile utilizing the adjusted output signals.

37. A method for calibrating projection data in a multislice computed tomography system, the system including an x-ray source and a detector array comprising a plurality of cells arranged in rows and columns and displaced along a z-axis, the detector array column cells arranged in channels, said method comprising the steps of:

determining an x-ray beam z-axis profile including obtaining signals from a select number of detector cells in at least one channel of the detector array;

determining a true x-ray flux utilizing detector gain profiles and the determined x-ray beam profile;

adjusting the projection data using the detector gain profiles and the determined x-ray flux profiles, including generating a gain profile for each non-selected detector cell;

wherein generating a gain profile for each non-selected detector cell comprises the step of determining a measured output signal, wherein the measured output signal, y', is:

$$y' = \sum_{i=0}^{M} g'_i \alpha'_i I'$$

where:

$g'_i$ = gain of cell i in detector channel;

$\alpha'_i$ = variation of flux in z direction on cell i;

$I'$ = average x-ray intensity of a non-fully sampled cell; and $M$ = number of cells that form a slice.

38. A method in accordance with claim 37 wherein generating the true x-ray flux for each non-selected detector cell further comprises the step of determining a true x-ray flux for the channel.

39. A method in accordance with claim 38 wherein the true x-ray flux for the channel is:

$$x' = \frac{\sum_{i=0}^{M} \alpha'_i}{\sum_{i=0}^{M} g'_i \alpha'_i} y'.$$

40. A method in accordance with claim 39 wherein each slice channel comprises four cells and wherein the measured output signal for each slice of each non-selected detector cell is:

$$y' = g'_0 \alpha'_0 I' + g'_1 \alpha'_1 I' + g'_2 \alpha'_2 I' + g'_3 \alpha'_3 I'.$$

41. A method in accordance with claim 39 wherein the true x-ray flux for the channel is:

$$x' = \frac{\alpha'_0 + \alpha'_1 + \alpha'_2 + \alpha'_3}{g'_0 \alpha'_0 + g'_1 \alpha'_1 + g'_2 \alpha'_2 + g'_3 \alpha'_3} y'.$$

42. A method in accordance with claim 41 wherein generating the x-ray flux profile for the non-selected detector cells comprises the step of creating a polynomial fit of the selected detector cell output signals.

43. A system for calibrating projection data for generating a tomographic image of an object, said system comprising an x-ray source and a detector array comprising a plurality of cells arranged in rows and columns and displaced along a z-axis, the detector array column cells being arranged in channels, said system configured to:

determine an x-ray beam z-axis profile;

determine a true x-ray flux utilizing detector gain profiles and the determined x-ray beam profile; and adjust the projection data using the detector gain profiles and the determined x-ray flux profiles;

wherein:

said system being configured to determine an x-ray beam z-axis profile comprises said system being configured to obtain signals from a select number of detector cells in at least one channel of the detector array;

said system being configured to adjust the projection data includes said system being configured to generate a gain profile for each non-selected detector cell; and said system being configured to generate a gain profile for each non-selected detector cell comprises said system being configured to determine a measured output signal, wherein the measured output signal, y', is:

$$y' = \sum_{i=0}^{M} g'_i \alpha'_i I'$$

where:

$g'_i$ = gain of cell i in detector channel;

$\alpha'_i$ = variation of flux in z direction on cell i;

$I'$ = average x-ray intensity of a non-fully sampled cell; and $M$ = number of cells that form a slice.

44. A system in accordance with claim 43 wherein said system being configured to generate the true x-ray flux for each non-selected detector cell comprises said system being configured to determine a true x-ray flux for the channel.

45. A system in accordance with claim 44 wherein the true x-ray flux for the channel is:

$$x' = \frac{\sum_{i=0}^{M} \alpha'_i}{\sum_{i=0}^{M} g'_i \alpha'_i} y'.$$

46. A system in accordance with claim 45 wherein each slice channel comprises four cells and wherein the measured output signal for each slice of each non-selected detector cell is:

$$y' = g'_0 \alpha'_0 l' + g'_1 \alpha'_1 l' + g'_2 \alpha'_2 l' + g'_3 \alpha'_3 l'.$$

47. A system in accordance with claim 45 wherein the true x-ray flux for the channel is:

$$x' = \frac{\alpha'_0 + \alpha'_1 + \alpha'_2 + \alpha'_3}{g'_0 \alpha'_0 + g'_1 \alpha'_1 + g'_2 \alpha'_2 + g'_3 \alpha'_3} y'.$$

48. A system in accordance with claim 47 wherein said system being configured to generate the x-ray flux profile for the non-selected detector cells comprises said system being configured to create a polynomial fit of the selected detector cell output signals.

* * * * *